(12) United States Patent
Oh et al.

(10) Patent No.: US 11,198,684 B2
(45) Date of Patent: Dec. 14, 2021

(54) INTERMEDIATES USEFUL FOR THE SYNTHESIS OF A SELECTIVE INHIBITOR AGAINST PROTEIN KINASE AND PROCESSES FOR PREPARING THE SAME

(71) Applicant: Yuhan Corporation, Seoul (KR)

(72) Inventors: Sang-Ho Oh, Gyeonggi-do (KR); Ja-Heouk Khoo, Gyeonggi-do (KR); Jong-Chul Lim, Gyeonggi-do (KR); Doo-Byung Lee, Gyeonggi-do (KR); Jung-Ae Lee, Seoul (KR); Jun-Sup Lee, Gyeonggi-do (KR); Hyun Ju, Gyeonggi-do (KR); Woo-Seob Shin, Gyeonggi-do (KR); Sang-Seol Jeon, Gyeonggi-do (KR)

(73) Assignee: Yuhan Corporation, Seoul (KR)

( * ) Notice: Subject to any disclaimer, the term of this patent is extended or adjusted under 35 U.S.C. 154(b) by 0 days.

(21) Appl. No.: 16/633,756

(22) PCT Filed: Jul. 25, 2018

(86) PCT No.: PCT/KR2018/008383
§ 371 (c)(1),
(2) Date: Jan. 24, 2020

(87) PCT Pub. No.: WO2019/022487
PCT Pub. Date: Jan. 31, 2019

(65) Prior Publication Data
US 2021/0155607 A1    May 27, 2021

(30) Foreign Application Priority Data
Jul. 28, 2017  (KR) .................. 10-2017-0096226

(51) Int. Cl.
*C07D 265/30* (2006.01)
*C07D 295/135* (2006.01)
*C07D 403/04* (2006.01)
*C07D 413/14* (2006.01)

(52) U.S. Cl.
CPC ....... *C07D 403/04* (2013.01); *C07D 295/135* (2013.01)

(58) Field of Classification Search
CPC .............. C07D 265/30; C07D 295/135; C07D 403/04; C07D 413/14
See application file for complete search history.

(56) References Cited

U.S. PATENT DOCUMENTS

2010/0029610 A1   2/2010  Singh et al.
2016/0102076 A1   4/2016  Suh et al.

FOREIGN PATENT DOCUMENTS

| CN | 104788427 A | 7/2015 |
| WO | 2011/060295 A1 | 5/2011 |
| WO | 2013/014448 A1 | 1/2013 |
| WO | 2013/096630 A1 | 6/2013 |
| WO | 2016/060443 A2 | 4/2016 |

OTHER PUBLICATIONS

Hu, J. et al., "Discovery of selective EGFRmodulator to inhibit L858R/T790M double mutants bearing a N-9-Diphenyl-9H-purin-2-amine scaffold", Bioorganic & Medicinal Chemistry, 2018, [Epub.] Feb. 17, 2018, vol. 26, pp. 1810-1822.

*Primary Examiner* — Brenda L Coleman
(74) *Attorney, Agent, or Firm* — BakerHostetler

(57) ABSTRACT

The present invention provides intermediates useful for the synthesis of an aminopyrimidine derivative or pharmaceutically acceptable salt thereof having a selective inhibitory activity against protein kinases, especially against the protein kinases for mutant epidermal growth factor receptors; and processes for preparing the same. And also, the present invention provides novel intermediates useful for said process and processes for preparing the same.

27 Claims, No Drawings

INTERMEDIATES USEFUL FOR THE SYNTHESIS OF A SELECTIVE INHIBITOR AGAINST PROTEIN KINASE AND PROCESSES FOR PREPARING THE SAME

CROSS-REFERENCE TO RELATED APPLICATIONS

This application is the National Stage of International Patent Application No. PCT/KR2018/008383 filed Jul. 25, 2018, which claims the benefit of Korean application number 10-2017-0096226, filed Jul. 28, 2017, the entire contents of both of which are incorporated herein by reference.

TECHNICAL FIELD

The present invention relates to intermediates useful for the synthesis of an aminopyrimidine derivative or pharmaceutically acceptable salt thereof having a selective inhibitory activity against protein kinase; and processes for preparing the same.

BACKGROUND ART

WO 2016/060443 has disclosed an aminopyrimidine derivative or pharmaceutically acceptable salt thereof having a selective inhibitory activity against protein kinases, especially against the protein kinases for mutant epidermal growth factor receptors. Said aminopyrimidine derivative or pharmaceutically acceptable salt thereof can provide an effective and safe therapy against non-small cell lung cancers. WO 2016/060443 has disclosed, as an aminopyrimidine derivative, for example N-(5-(4-(4-((dimethylamino)methyl)-3-phenyl-1H-pyrazol-1-yl)pyrimidin-2-ylamino)-4-methoxy-2-morpholinophenyl)acrylamide of the following Formula 1 and a process for preparing the same.

<Formula 1>

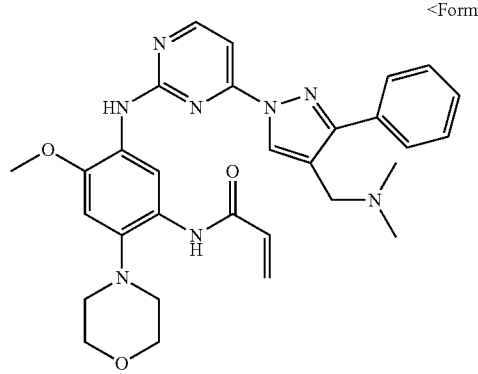

WO 2016/060443 has also disclosed a process for preparing the aminopyrimidine derivative of Formula (I), for example a process according to the following Reaction Scheme. In the following Reaction Scheme, $R_1$ may be methoxy, $R_2$ may be hydrogen, $R_3$ may be morpholinyl, $R_4$ may be hydrogen, $R_5$ may be phenyl, $R_6$ may be hydrogen, and $R_7$ may be dimethylamino.

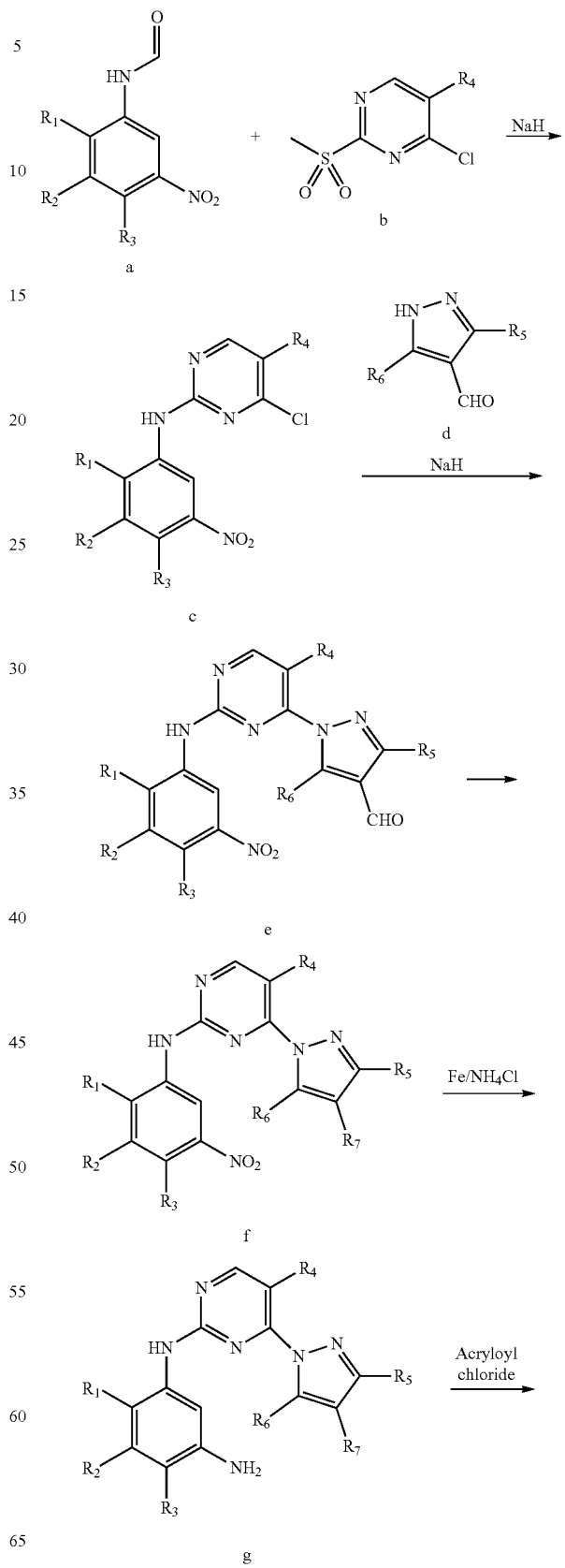

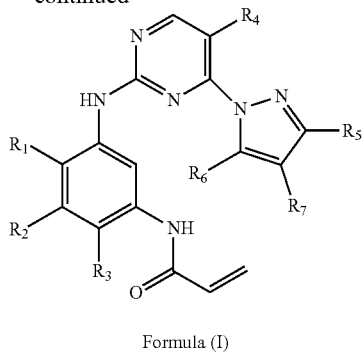

Formula (I)

Specifically, the process for preparing the compound of Formula (I) according to the above Reaction Scheme comprises reacting a compound of Formula (a) with a compound of Formula (b) by use of sodium hydride to obtain a compound of Formula (c); reacting the compound of Formula (c) with a compound of Formula (d) by use of sodium hydride to obtain a compound of Formula (e); performing reductive amination of the compound of Formula (e) to obtain a compound of Formula (f); reducing the compound of Formula (f) by use of iron and ammonium chloride to obtain a compound of Formula (g); and reacting the compound of Formula (g) with acryloyl chloride to obtain a compound of Formula (I).

Said process includes the reactions using sodium hydride, in order to prepare the compound of Formula (c) and the compound of Formula (e). However, since sodium hydride has a high possibility of fire and explosion, there is a problem that it is difficult to use in industrial mass production.

And also, said process includes the use of iron in the step for reducing the nitro group of the compound of Formula (f) to the amino group thereof. However, the use of iron may cause corrosion and contamination in a reactor, which makes it difficult to be applied to mass production. Further, during the reduction using iron and ammonium chloride to obtain the compound of the Formula (g), unknown tars and degradation products are produced; and the product (i.e., the compound of the Formula (g)) is obtained in black color. Therefore, in order to obtain the final product, the compound of formula (I), having a suitable purity, it is required to perform the purification process by column chromatography which is difficult to apply to mass production.

In addition, since acryloyl chloride used in the final step for preparing the compound of Formula (I) has low stability, it is difficult to handle at the production site. And also, since various degradation products are produced during the reaction of the compound of formula (g) with acryloyl chloride, it is difficult to prepare the compound of Formula (I) having a suitable purity.

DISCLOSURE

Technical Problem

The present invention provides an improved process which is suitable for industrial mass production and which is able to produce N-(5-(4-(4-((dimethylamino)methyl)-3-phenyl-1H-pyrazol-1-yl)pyrimidin-2-ylamino)-4-methoxy-2-morpholinophenyl)acrylamide (the compound of Formula 1) or a pharmaceutically acceptable salt thereof with high purity and yield. Especially, the present invention provides intermediates useful for the synthesis of the compound of Formula 1 or a pharmaceutically acceptable salt thereof and processes for preparing the same.

And also, the present invention provides novel intermediates useful for said process and processes for preparing the same.

Technical Solution

According to an aspect of the present invention, there is provided a process for preparing N-(5-(4-(4-formyl-3-phenyl-1H-pyrazol-1-yl)pyrimidin-2-ylamino)-4-methoxy-2-morpholinophenyl)acrylamide (the compound of Formula 2), the process comprising reacting tert-butyl (5-acrylamido-2-methoxy-4-morpholinophenyl)carbamate (the compound of Formula 4) or N-(5-amino-4-methoxy-2-morpholinophenyl)acrylamide (the compound of Formula 3) with a compound of Formula 13:

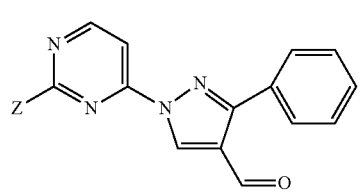

<Formula 13> wherein, Z is halogen.

The N-(5-amino-4-methoxy-2-morpholinophenyl)acrylamide (the compound of Formula 3) may be obtained by reacting tert-butyl (5-acrylamido-2-methoxy-4-morpholinophenyl)carbamate (the compound of Formula 4) with an acid. For example, the reacting of tert-butyl (5-acrylamido-2-methoxy-4-morpholinophenyl)carbamate (the compound of Formula 4) with the compound of Formula 13 may be carried out in the presence of an acid. And also, for example, the reacting of N-(5-amino-4-methoxy-2-morpholinophenyl)acrylamide (the compound of Formula 3) with the compound of Formula 13 may be carried out in the presences of a metal catalyst, a ligand, and a base. And also, for example, the reacting of N-(5-amino-4-methoxy-2-morpholinophenyl)acrylamide (the compound of Formula 3) with the compound of Formula 13 may be carried out in the presence of an acid.

In an embodiment, the tert-butyl (5-acrylamido-2-methoxy-4-morpholinophenyl)carbamate (the compound of Formula 4) may be obtained by a process comprising (i) reacting tert-butyl (5-amino-2-methoxy-4-morpholinophenyl)carbamate (the compound of Formula 6) with a compound of Formula 11 to form a compound of Formula 5; and (ii) reacting the compound of Formula 5 with a base to obtain tert-butyl (5-acrylamido-2-methoxy-4-morpholinophenyl)carbamate (the compound of Formula 4):

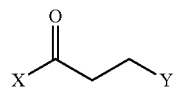

<Formula 11>

<Formula 5>

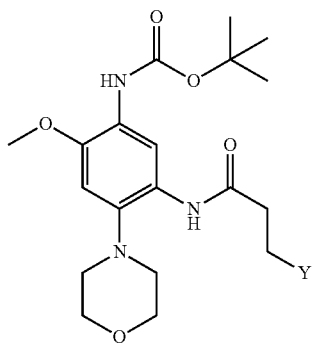

wherein, X and Y are, independently of each other, halogen.

In another embodiment, the tert-butyl (5-amino-2-methoxy-4-morpholinophenyl)carbamate (the compound of Formula 6) may be obtained by performing a reduction of tert-butyl (2-methoxy-4-morpholino-5-nitrophenyl)carbamate (the compound of Formula 7). The tert-butyl (2-methoxy-4-morpholino-5-nitrophenyl)carbamate (the compound of Formula 7) may be obtained by reacting tert-butyl (4-fluoro-2-methoxy-5-nitrophenyl)carbamate (the compound of Formula 8) with morpholine. The tert-butyl (4-fluoro-2-methoxy-5-nitrophenyl)carbamate (the compound of Formula 8) is obtained by reacting 4-fluoro-2-methoxy-5-nitroaniline (the compound of Formula 9) with dibutyl dicarbonate.

In a still another embodiment, the compound of Formula 13 may be obtained by reacting a compound of Formula 14 with 3-phenyl-1H-pyrazole-4-carbaldehyde (the compound of Formula 15).

<Formula 14>

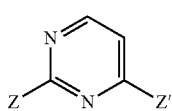

wherein, Z and Z' are, independently of each other, halogen.

In another aspect of the present invention, there is provided N-(5-amino-4-methoxy-2-morpholinophenyl)acrylamide (the compound of Formula 3).

In still another aspect of the present invention, there is provided tert-butyl (5-acrylamido-2-methoxy-4-morpholinophenyl)carbamate (the compound of Formula 4).

In still another aspect of the present invention, there is provided a compound of Formula 5 or salt thereof:

<Formula 5>

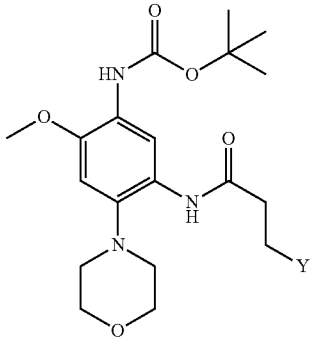

wherein, Y is halogen.

In still another aspect of the present invention, there is provided tert-butyl (5-amino-2-methoxy-4-morpholinophenyl)carbamate (the compound of Formula 6).

In still another aspect of the present invention, there is provided tert-butyl (2-methoxy-4-morpholino-5-nitrophenyl)carbamate (the compound of Formula 7).

Advantageous Effects

The process of the present invention can effectively solve the problems involved in the prior art process, by preparing N-(5-(4-(4-(((dimethylamino)methyl)-3-phenyl-1H-pyrazol-1-yl)pyrimidin-2-ylamino)-4-methoxy-2-morpholinophenyl)acrylamide (the compound of Formula 1) through novel intermediates, i.e., the compounds of Formulas 2, 3, 4, 5, 6 and 7. That is, the process of the present invention includes preparing the compound of Formula 5 from the compound of Formula 6; and then converting the compound of Formula 5 to the compound of Formula 4, alternatively followed by converting the compound of Formula 4 to the compound of Formula 3, thereby being able to avoid the use of acryloyl chloride. And also, in the process of the present invention, the removal and control of impurities can be easily performed. In addition, since the present invention may avoid the use of iron and ammonium chloride in the step for preparing the compound of Formula 6 (i.e., in the reduction step), said process is able to solve the problems of corrosion and contamination in a reactor which is caused by the use of iron; and therefore is suitable for industrial mass production.

BEST MODE FOR CARRYING OUT THE INVENTION

The present invention provides a novel process for preparing N-(5-(4-(4-formyl-3-phenyl-1H-pyrazol-1-yl)pyrimidin-2-ylamino)-4-methoxy-2-morpholinophenyl)acrylamide (the compound of Formula 2), which is one of the key synthetic intermediates for N-(5-(4-(4-(((dimethylamino)methyl)-3-phenyl-1H-pyrazol-1-yl)pyrimidin-2-yl)amino)-4-methoxy-2-morpholinophenyl)acrylamide or a pharmaceutically acceptable salt thereof (the compound of Formula 1). That is, the present invention provides a novel process for preparing the compound of Formula 2 through novel intermediates; and a process for preparing the compound of Formula 1 or a pharmaceutically acceptable salt thereof using the same. The overall reaction scheme of the process of the present invention is represented as the following Reaction Scheme 1.

<Reaction Scheme 1>
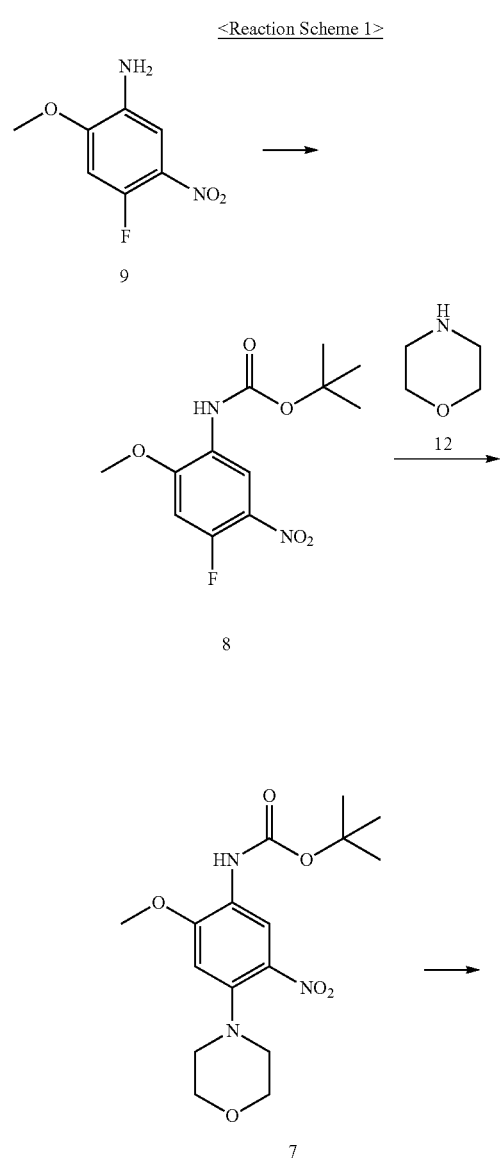
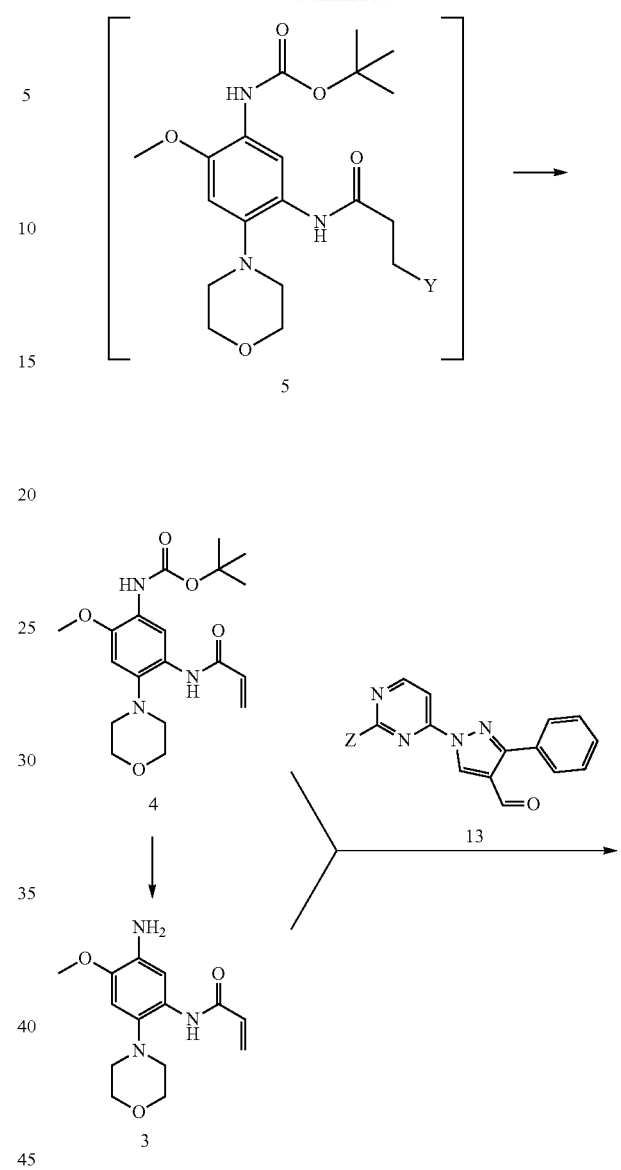
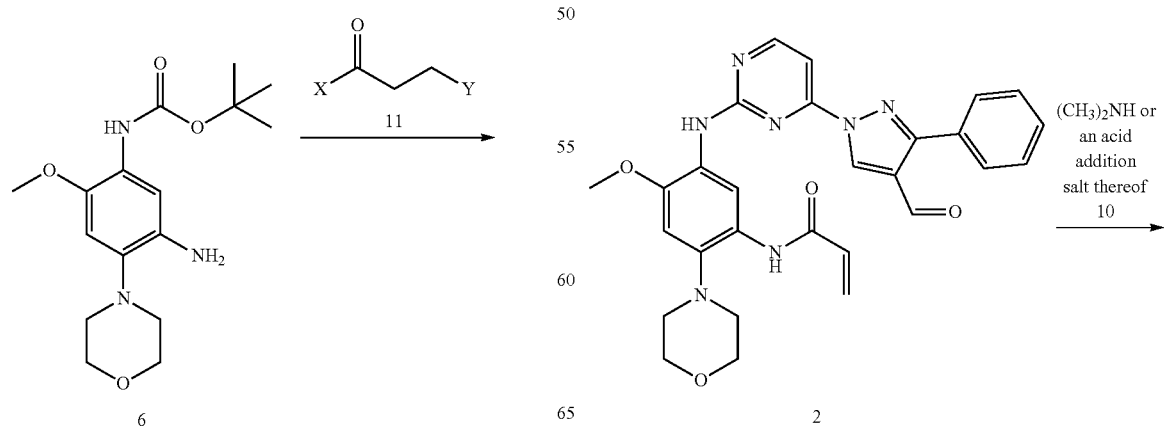

-continued

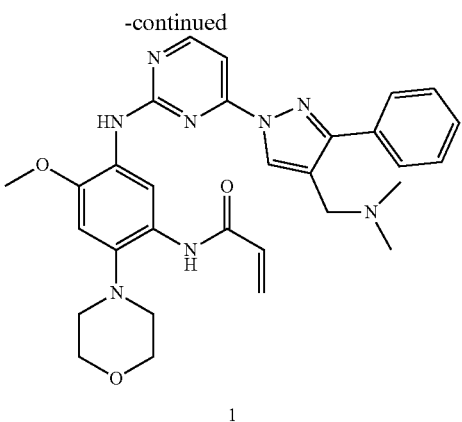

1

In the Reaction Scheme 1, X, Y and Z are, independently of each other, halogen.

Hereinafter, the processes of the present invention will be described in detail with reference to the respective steps of the Reaction Scheme 1.

The present invention provides a process for preparing N-(5-(4-(4-formyl-3-phenyl-1H-pyrazol-1-yl)pyrimidin-2-ylamino)-4-methoxy-2-morpholinophenyl)acrylamide (the compound of Formula 2), the process comprising reacting tert-butyl (5-acrylamido-2-methoxy-4-morpholinophenyl) carbamate (the compound of Formula 4) or N-(5-amino-4-methoxy-2-morpholinophenyl)acrylamide (the compound of Formula 3) with a compound of Formula 13:

<Formula 13>

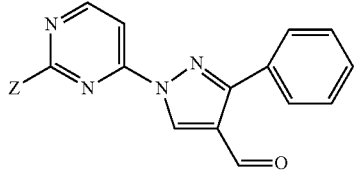

wherein, Z is halogen.

In the process of the present invention, the N-(5-amino-4-methoxy-2-morpholinophenyl)acrylamide (the compound of Formula 3) may be obtained by reacting tert-butyl (5-acrylamido-2-methoxy-4-morpholinophenyl)carbamate (the compound of Formula 4) with an acid. The acid may be one or more selected from the group consisting of hydrochloric acid, sulfuric acid, phosphoric acid, nitric acid, acetic acid, formic acid, sulfonic acid and p-toluenesulfonic acid. Preferably, the acid may be p-toluenesulfonic acid or hydrochloric acid. Although the amount of the acid to be used is not particularly limited, the acid may be used for example in a ratio ranging from 1 to 10 equivalents per 1 equivalent of the compound of Formula 4. And also, the reacting of the compound of Formula 4 with the acid may be carried out in the presence of one or more solvent(s) selected from the group consisting of dichloromethane, dichloroethane, dimethylformamide, dimethylacetamide, dimethyl sulfoxide, tetrahydrofuran, $C_1$~$C_5$ alcohol, ethyl acetate, and toluene. Preferably, the solvent may be $C_1$~$C_5$ alcohol, such as methanol, ethanol, isopropyl alcohol, or butanol.

The reacting of tert-butyl (5-acrylamido-2-methoxy-4-morpholinophenyl)carbamate (the compound of Formula 4) with the compound of Formula 13 may be carried out in the presence of an acid. The acid may be one or more selected from the group consisting of hydrochloric acid, sulfuric acid, phosphoric acid, nitric acid, acetic acid, formic acid, sulfonic acid and p-toluenesulfonic acid. Preferably, the acid may be p-toluenesulfonic acid or hydrochloric acid. Although the amount of the acid to be used is not particularly limited, the acid may be used for example in a ratio ranging from 0.01 to 1 equivalent per 1 equivalent of the compound of Formula 4. And also, the reacting of the compound of Formula 4 with the compound of Formula 13 may be carried out in the presence of one or more solvent(s) selected from the group consisting of dichloromethane, dichloroethane, dimethylformamide, dimethylacetamide, dimethyl sulfoxide, tetrahydrofuran, $C_1$~$C_5$ alcohol, ethyl acetate, and toluene. Preferably, the solvent may be $C_1$~$C_5$ alcohol, such as methanol, ethanol, isopropyl alcohol, or butanol.

And also, the reacting of N-(5-amino-4-methoxy-2-morpholinophenyl)acrylamide (the compound of Formula 3) with the compound of Formula 13 may be carried out in the presences of a metal catalyst, a ligand, and a base. The metal catalyst may be one or more selected from the group consisting of palladium, copper, iron, cadmium, zinc, and nickel. Preferably, the metal catalyst may be palladium acetate, palladium acetylacetonate, bis(dibenzylideneacetone)palladium, or tris(dibenzylideneacetone)dipalladium. The ligand may be one or more selected from the group consisting of 2,2'-bis(diphenylphosphino)-1,1'-binaphthalene (BINAP), 1,1'-bis(diphenylphosphino)ferrocene (DPPF), and 4,5-bis(diphenylphosphino)-9,9-dimethylxanthene (Xantphos). Preferably, the ligand may be 4,5-bis (diphenylphosphino)-9,9-dimethylxanthene (Xantphos). The metal catalyst and the ligand may be used in a ratio ranging from 0.05 to 1 equivalent per 1 equivalent of the compound of Formula 3, although the amounts thereof may vary according thereto. And also, the base may be one or more selected from the group consisting of potassium tert-butoxide, sodium hydroxide, potassium hydroxide, sodium hydride, sodium carbonate, potassium carbonate, potassium phosphate (including potassium phosphate monobasic, potassium phosphate dibasic, and potassium phosphate tribasic), sodium phosphate (including sodium phosphate monobasic, sodium phosphate dibasic, and sodium phosphate tribasic), cesium carbonate, 1,8-diazabicyclo[5.4.0] undec-7-ene (DBU), 1,4-diazabicyclo[2.2.2]octane (DABCO), 1,5-diazabicyclo[4.3.0]non-5-ene (DBN), pyridine, triethylamine, diisopropylamine, and diisopropylethylamine. And also, the reacting of the compound of Formula 3 with the compound of Formula 13 may be carried out in the presence of one or more solvent(s) selected from the group consisting of dichloromethane, dichloroethane, dimethylformamide, dimethylacetamide, dimethyl sulfoxide, tetrahydrofuran, $C_1$~$C_5$ alcohol, ethyl acetate, and toluene. The solvent may be preferably $C_1$~$C_5$ alcohol, such as methanol, ethanol, isopropyl alcohol, or butanol, more preferably tetrahydrofuran. And also, the reacting of the compound of Formula 3 with the compound of Formula 13 may be carried out at a temperature ranging from 40 to 150° C., preferably 70 to 90° C.

And also, the reacting of the compound of Formula 3 with the compound of Formula 13 may be carried out in the presence of an acid. The acid may be one or more selected from the group consisting of hydrochloric acid, sulfuric acid, phosphoric acid, nitric acid, acetic acid, formic acid, sulfonic acid and p-toluenesulfonic acid. Preferably, the acid may be p-toluenesulfonic acid or hydrochloric acid. Although the amount of the acid to be used is not particularly limited, the acid may be used for example in a ratio ranging from 0.01 to 1 equivalent per 1 equivalent of the compound of Formula 3. And also, the reacting of the compound of Formula 3 with the compound of Formula 13 may be carried out in the presence of one or more solvent(s) selected from the group consisting of dichloromethane, dichloroethane, dimethylformamide, dimethylacetamide, dimethyl sulfoxide, tetrahydrofuran, $C_1$~$C_5$ alcohol, ethyl acetate, and toluene. Preferably, the solvent may be $C_1$~$C_5$ alcohol, such as methanol, ethanol, isopropyl alcohol, or butanol.

In the process of the present invention, the tert-butyl (5-acrylamido-2-methoxy-4-morpholinophenyl)carbamate (the compound of Formula 4) may be obtained by a process comprising (i) reacting tert-butyl (5-amino-2-methoxy-4-morpholinophenyl)carbamate (the compound of Formula 6) with a compound of Formula 11 to form a compound of Formula 5; and (ii) reacting the compound of Formula 5 with a base to obtain tert-butyl (5-acrylamido-2-methoxy-4-morpholinophenyl)carbamate (the compound of Formula 4):

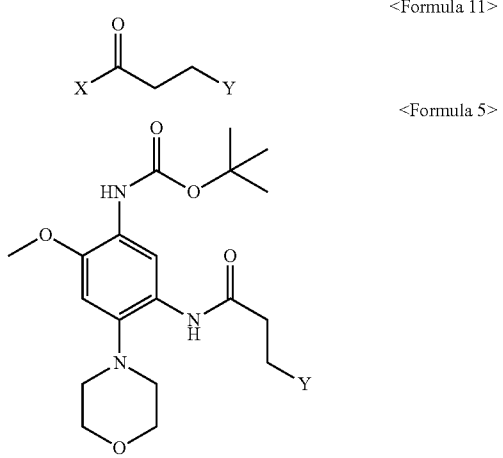

wherein, X and Y are, independently of each other, halogen.

In an embodiment of the process of the present invention, Step (i) and Step (ii) may be carried out in a one-pot reaction, without isolating the compound of Formula 5. Therefore, the process of the present invention is suitable for industrial mass production.

The reacting of Step (i), i.e., the reaction of the compound of Formula 6 with the compound of Formula 11, may be carried out in the presence of one or more base(s) selected from the group consisting of potassium tert-butoxide, sodium hydroxide, potassium hydroxide, lithium hydroxide, sodium hydride, sodium carbonate, sodium bicarbonate, potassium carbonate, potassium phosphate (including potassium phosphate monobasic, potassium phosphate dibasic, and potassium phosphate tribasic), sodium phosphate (including sodium phosphate monobasic, sodium phosphate dibasic, and sodium phosphate tribasic), 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, triethylamine, diisopropylamine and diisopropylethylamine. The base may be used in an amount ranging from 1 to 5 equivalents, preferably from 1 to 3 equivalents, per 1 equivalent of the compound of Formula 6. And also, the reaction may be carried out in the presence of one or more solvent(s) selected from the group consisting of acetone, acetonitrile, methyl ethyl ketone, dimethylformamide, dimethylacetamide, dichloromethane, dimethyl sulfoxide, dimethylsulfonamide, tetrahydrofuran, hexamethylphosphoramide, $C_1$~$C_5$ alcohol, dimethyl ether, diethyl ether, diisopropyl ether, ethyl acetate, dimethoxyethane and toluene. Preferably, the solvent may be acetone, acetonitrile, methyl ethyl ketone, or $C_1$~$C_5$ alcohol (such as methanol, ethanol, propanol, isopropyl alcohol, butanol, and so on). More preferably, the solvent may be acetonitrile. The reaction may be carried out at a temperature ranging from 0 to 100° C., preferably from 10 to 30° C.

In the reacting of Step (ii), i.e., the reaction of the compound of Formula 5 with a base, the base may be one or more selected from the group consisting of potassium tert-butoxide, sodium hydroxide, potassium hydroxide, lithium hydroxide, sodium hydride, sodium carbonate, sodium bicarbonate, potassium carbonate, potassium phosphate (including potassium phosphate monobasic, potassium phosphate dibasic, and potassium phosphate tribasic), sodium phosphate (including sodium phosphate monobasic, sodium phosphate dibasic, and sodium phosphate tribasic), 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, triethylamine, diisopropylamine and diisopropylethylamine. The base may be preferably sodium hydroxide, triethylamine or diisopropylamine, more preferably triethylamine. The base may be used in an amount ranging from 1 to 20 equivalents, preferably from 5 to 10 equivalents, per 1 equivalent of the compound of Formula 6. And also, the reaction may be carried out in the presence of a solvent selected from the group consisting of acetonitrile, methyl ethyl ketone, acetone, methyl isobutyl ketone, dichloromethane, dichloroethane, dimethylformamide, dimethylacetamide, dimethyl sulfoxide, tetrahydrofuran, $C_1$~$C_5$ alcohol, toluene, ethyl acetate, isopropyl acetate, diethyl ether, water and a mixture thereof. Preferably, the solvent may be selected from the group consisting of acetonitrile, tetrahydrofuran, methyl ethyl ketone, acetone, dichloromethane, water and a mixture thereof. More preferably, the solvent may be acetonitrile. The reacting of the compound of Formula 5 with the base may be carried out at a temperature ranging from 40 to 150° C., preferably at a temperature ranging from 60 to 100° C., more preferably at the reflux temperature of the used solvent.

In the process of the present invention, the tert-butyl (5-amino-2-methoxy-4-morpholinophenyl)carbamate (the compound of Formula 6) may be obtained by performing a reduction of tert-butyl (2-methoxy-4-morpholino-5-nitrophenyl)carbamate (the compound of Formula 7). The reduction may be carried out with a reducing agent selected from the group consisting of formic acid and ammonium formate. The reducing agent may be in amount ranging from 1 to 15 equivalents per 1 equivalent of the compound of Formula 7. And also, the reduction may be carried out in the presence of a catalyst selected from the group consisting of palladium, palladium/carbon, zinc, copper, magnesium, and platinum, preferably in the presence of palladium/carbon. The reaction may be carried out in the presence of an inert solvent, for example in the presence of one or more solvent(s) selected from the group consisting of dimethylformamide, dimethylacetamide, dichloromethane, dimethyl sulfoxide, tetrahydrofuran, hexamethylphosphoramide, $C_1$~$C_5$ alcohol, diethyl ether, ethyl acetate, acetonitrile and acetone. Preferably, the solvent may be tetrahydrofuran or ethanol. And also, the reaction may be carried out at a temperature ranging from 0 to 50° C., preferably 20 to 30° C.

In the process of the present invention, the tert-butyl (2-methoxy-4-morpholino-5-nitrophenyl)carbamate (the compound of Formula 7) may be obtained by reacting tert-butyl (4-fluoro-2-methoxy-5-nitrophenyl)carbamate (the compound of Formula 8) with morpholine. The reacting of the compound of Formula 8 with morpholine may be carried out in the presence of one or more base(s) selected from the group consisting of sodium hydride, sodium $C_1$~$C_6$ alkoxide, potassium $C_1$~$C_6$ alkoxide, sodium carbonate, potassium carbonate, lithium carbonate, cesium carbonate, sodium bicarbonate, potassium bicarbonate, potassium phosphate, 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, dimethylaminopyridine, triethylamine, and diisopropylethylamine. Preferably, the base may be triethylamine or diisopropylethylamine. And also, the reacting of the compound of Formula 8 with morpholine may be carried out in the presence of an inert solvent, for example in the presence of one or more solvent(s) selected from the group consisting of dimethylformamide, dimethylacetamide, dichloromethane, dimethyl sulfoxide, tetrahydrofuran, hexamethylphosphoramide, $C_1$~$C_5$ alcohol, diethyl ether, ethyl acetate, acetonitrile and acetone. Preferably, the solvent may be acetonitrile and/or tetrahydrofuran. And also, the reaction may be carried out at a temperature ranging from 0 to 100° C., preferably from 70 to 80° C.

In the process of the present invention, the tert-butyl (4-fluoro-2-methoxy-5-nitrophenyl)carbamate (the compound of Formula 8) is obtained by reacting 4-fluoro-2-methoxy-5-nitroaniline (the compound of Formula 9) with dibutyl dicarbonate. The reacting of the compound of Formula 9 with dibutyl dicarbonate may be carried out in the presence of one or more base(s) selected from the group consisting of sodium hydride, sodium $C_1$~$C_6$ alkoxide, potassium $C_1$~$C_6$ alkoxide, sodium carbonate, potassium carbonate, lithium carbonate, cesium carbonate, sodium bicarbonate, potassium bicarbonate, potassium phosphate, 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, dimethylaminopyridine and triethylamine. Preferably, the base may be triethylamine. And also, in order to improve the reactivity, 4-dimethylaminopyridine may be additional used. The reaction may be carried out in the presence of an inert solvent, for example in the presence of one or more solvent(s) selected from the group consisting of dimethylformamide, dimethylacetamide, dichloromethane, dimethyl sulfoxide, tetrahydrofuran, hexamethylphosphoramide, $C_1$~$C_5$ alcohol, diethyl ether, ethyl acetate, acetonitrile and acetone. Preferably, the solvent may be dichloromethane. And also, the reaction may be carried out at a temperature ranging from 0 to 50° C., preferably from 20 to 30° C.

In an embodiment, the compound of Formula 13 used as an intermediate in Reaction Scheme 1 may be obtained by reacting a compound of Formula 14 with 3-phenyl-1H-pyrazole-4-carbaldehyde (the compound of Formula 15).

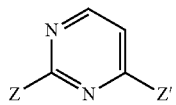

<Formula 14> wherein, Z and Z' are, independently of each other, halogen.

The reacting the compound of Formula 14 with the compound of Formula 15 may be carried out in the presence of one or more base(s) selected from the group consisting of sodium hydride, sodium $C_1$~$C_6$ alkoxide, potassium $C_1$~$C_6$ alkoxide, sodium carbonate, potassium carbonate, lithium carbonate, cesium carbonate, sodium bicarbonate, potassium bicarbonate, potassium phosphate, 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, dimethylaminopyridine and triethylamine. Preferably, the base may be potassium carbonate. The reaction may be carried out in the presence of an inert solvent, for example in the presence of one or more solvent(s) selected from the group consisting of dimethylformamide, dimethylacetamide, dichloromethane, dimethyl sulfoxide, tetrahydrofuran, hexamethylphosphoramide, $C_1$~$C_5$ alcohol, diethyl ether, ethyl acetate, acetonitrile and acetone. Preferably, the solvent may be dimethylformamide. And also, the reaction may be carried out at a temperature ranging from 0 to 50° C., preferably from 0 to 10° C.

The N-(5-(4-(4-formyl-3-phenyl-1H-pyrazol-1-yl)pyrimidin-2-ylamino)-4-methoxy-2-morpholinophenyl)acrylamide (the compound of Formula 2) obtained by the above-mentioned process of the present invention may be converted to the compound of Formula 1 or a pharmaceutically acceptable salt thereof, according to the above Reaction Scheme 1. For example, the conversion may comprise (a) reacting the compound of formula 2 with dimethylamine or an acid addition salt thereof in the presences of a reducing agent and a base to form N-(5-(4-(4-((dimethylamino)methyl)-3-phenyl-1H-pyrazol-1-yl)pyrimidin-2-ylamino)-4-methoxy-2-morpholinophenyl)acrylamide (the compound of formula 1); and (b) isolating the N-(5-(4-(4-((dimethylamino)methyl)-3-phenyl-1H-pyrazol-1-yl)pyrimidin-2-ylamino)-4-methoxy-2-morpholinophenyl)acrylamide (the compound of formula 1) from the reaction mixture of Step (a).

The reaction of Step (a) is a reductive amination. The reducing agent used in said reductive amination may be one or more selected from the group consisting of sodium triacetoxyborohydride, sodium cyanoborohydride, and sodium borohydride. Preferably, the reducing agent may be sodium triacetoxyborohydride. The reducing agent may be used in an amount ranging from 1 to 5 equivalents, preferably from 1 to 3 equivalents, per 1 equivalent of the compound of Formula 2, although the amount thereof may vary according to the reducing agents. The base used in said reaction may be one or more selected from the group consisting of sodium carbonate, sodium bicarbonate, potassium carbonate, potassium phosphate (including potassium phosphate monobasic, potassium phosphate dibasic, and potassium phosphate tribasic), sodium phosphate (including sodium phosphate monobasic, sodium phosphate dibasic, and sodium phosphate tribasic), 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, triethylamine, diisopropylamine and diisopropylethylamine. Said reductive amination may be carried out in the presence of one or more solvent(s) selected from the group consisting of dimethylacetamide, dimethylformamide, dichloromethane, tetrahydrofuran, acetonitrile and ethyl acetate. And also, said reaction may be carried out at a temperature ranging from 0 to 50° C., preferably from 20 to 30° C. Therefore, the process of the present invention may be carried out under a mild condition; and thus is suitable for industrial mass production.

The isolating of Step (b) may be carried out by crystallization from the reaction mixture of Step (a). For example, the isolating of Step (b) may be performed by crystallization through adding an antisolvent to the reaction mixture of Step (a). The antisolvent may be $C_1$~$C_5$ alcohol (for example, methanol, ethanol, isopropanol, butanol, and so on), water, or a mixture thereof, preferably water. Although the amount of the antisolvent to be used is not particularly limited, the antisolvent may be used for example in a weight ratio ranging from 2 to 20 times, preferably from 3 to 10 times, based on the compound of Formula 2. The isolating step may be also carried out at a temperature ranging from 0 to 40° C., preferably from 20 to 30° C. Therefore, the process of the present invention may be carried out under a mild condition; and thus is suitable for industrial mass production.

The present invention includes, within its scope, novel intermediates useful for said novel processes.

That is, the present invention provides N-(5-amino-4-methoxy-2-morpholinophenyl)acrylamide (the compound of Formula 3).

And also, the present invention provides tert-butyl (5-acrylamido-2-methoxy-4-morpholinophenyl)carbamate (the compound of Formula 4).

And also, the present invention provides a compound of Formula 5 or salt thereof:

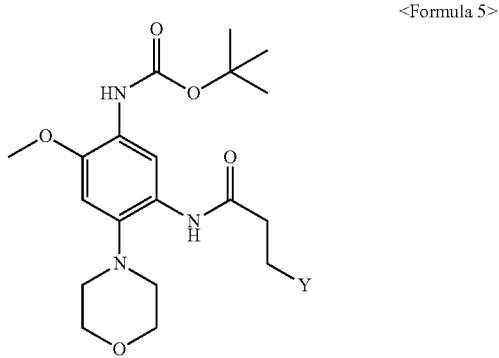

<Formula 5> wherein, Y is halogen.

And also, the present invention provides tert-butyl (5-amino-2-methoxy-4-morpholinophenyl)carbamate (the compound of Formula 6).

And also, the present invention provides tert-butyl (2-methoxy-4-morpholino-5-nitrophenyl)carbamate (the compound of Formula 7).

The following examples are provided for illustration purposes only, and are not intended to limit the scope of the invention.

Example 1. Preparation of 1-(2-chloropyrimidin-4-yl)-3-phenyl-1H-pyrazole-4-carbaldehyde (Compound 13)

A mixture of 2,4-dichloropyrimidine (30.0 g, 0.201 mol), potassium carbonate (55.6 g, 0.402 mol), and dimethylformamide (180.0 mL) was cooled to 0-5° C. and then 3-phenyl-1H-pyrazole-4-carbaldehyde (41.6 g, 0.242 mol) was added thereto. The reaction mixture was stirred for 15 hours and then purified water (1.2 L) was added thereto. The resulting solid was filtered and then dried in vacuo to obtain 48.8 g of the titled compound. (Yield: 85.1%)

$^1$H-NMR (400 MHz, DMSO) δ 10.08 (s, 1H), 9.52 (s, 1H), 8.94-8.95 (d, 1H), 8.09-8.10 (d, 1H), 7.96-8.01 (m, 2H), 7.52-7.55 (m, 3H)

Example 2. Preparation of tert-butyl (4-fluoro-2-methoxy-5-nitrophenyl)carbamate (Compound 8)

A mixture of 4-fluoro-2-methoxy-5-nitroaniline (60.0 g, 0.322 mol) and dichloromethane (500.0 mL) was cooled to 0-5° C. A solution of dibutyl dicarbonate (91.5 g, 0.419 mol) in dichloromethane (120.0 mL), 4-dimethylaminopyridine (3.9 g, 0.032 mol), and triethylamine (65.2 g, 0.645 mol) were added to the mixture. The reaction mixture was stirred at 20-30° C. for 4 hours and then concentrated under reduced pressure to obtain 92.3 g of the titled compound. (Yield: 100.0%)

$^1$H-NMR (400 MHz, CDCl$_3$) δ 8.88 (d, 1H), 6.98 (s, 1H), 6.72 (d, 1H), 3.95 (s, 3H), 1.54 (s, 9H)

Example 3. Preparation of tert-butyl (2-methoxy-4-morpholino-5-nitrophenyl)carbamate (Compound 7)

A mixture of tert-butyl (4-fluoro-2-methoxy-5-nitrophenyl)carbamate (92.3 g, 0.322 mol), acetonitrile (600.0 mL), diisopropylethylamine (54.1 g, 0.419 mol), and morpholine (36.5 g, 0.419 mol) was refluxed under stirring for about 3 hours. The reaction mixture was concentrated under reduced pressure to obtain 99.0 g of the titled compound.

$^1$H-NMR (400 MHz, CDCl$_3$) δ 8.71 (s, 1H), 6.92 (s, 1H), 6.57 (s, 1H), 3.95 (s, 3H), 3.86 (t, 4H), 3.03 (t, 4H), 1.53 (s, 9H)

Example 4. Preparation of tert-butyl (5-amino-2-methoxy-4-morpholinophenyl)carbamate (Compound 6)

A mixture of tert-butyl (2-methoxy-4-morpholino-5-nitrophenyl)carbamate (120.0 g, 0.340 mol), tetrahydrofuran (1.2 L), ethanol (1.2 L), ammonium formate (180.0 g, 2.854 mol), and palladium/carbon (12.0 g) was stirred at 15-25° C. for 2 hours and then filtered through a celite pad. The resulting filtrate was concentrated under reduced pressure. Dichloromethane (1.4 L) and purified water (1.0 L) were added to the resulting residue, which was then stirred for 1 hour. The separated organic layer was concentrated under reduced pressure to obtain 100.5 g of the titled compound. (Yield: 91.5%)

$^1$H-NMR (400 MHz, CDCl$_3$) δ 7.59 (s, 1H), 6.97 (s, 1H), 6.60 (s, 1H), 3.95 (t, 4H), 3.80 (s, 3H), 2.87 (t, 4H), 1.51 (s, 9H)

Example 5. Preparation of tert-butyl (5-acrylamido-2-methoxy-4-morpholinophenyl)carbamate (Compound 4)

A mixture of tert-butyl (5-amino-2-methoxy-4-morpholinophenyl)carbamate (10.0 g, 0.031 mol), acetonitrile (100.0 mL), sodium bicarbonate (7.8 g, 0.093 mol), and 3-chloropropionyl chloride (5.1 g, 0.040 mol) was stirred at 20-30° C. for 1 hour to form tert-butyl (5-(3-chloropropaneamido)-2-methoxy-4-morpholinophenyl)carbamate (Compound 5). Triethylamine (31.3 g, 0.309 mol) was added to the reaction mixture, which was refluxed under stirring for about 7 hours, cooled to 20-30° C., and then filtered. The resulting filtrate was concentrated under reduced pressure to obtain titled 11.5 g of the titled compound. (Yield: 98.5%)

$^1$H-NMR (400 MHz, CDCl$_3$) δ 9.11 (s, 1H), 8.38 (s, 1H), 6.91 (s, 1H), 6.69 (s, 1H), 6.41 (d, 1H), 6.27 (t, 1H), 5.74 (d, 1H), 3.85 (m, 7H), 2.84 (t, 4H), 1.52 (s, 9H)

Example 6. Preparation of N-(5-amino-4-methoxy-2-morpholinophenyl)acrylamide (Compound 3)

A mixture of tert-butyl (5-acrylamido-2-methoxy-4-morpholinophenyl)carbamate (38.0 g, 0.100 mol), ethanol (380.0 mL), and conc. hydrochloric acid (52.4 g, 0.503 mol) was stirred at 50-60° C. for 2 hours. The reaction mixture was cooled to 20-30° C. Dichloromethane (500 mL), purified water (500 mL), and sodium bicarbonate (63.4 g, 0.755 mol) were added to the reaction mixture, which was then stirred for 1 hour. The separated organic layer was concentrated under reduced pressure to obtain 25.4 g of the titled compound. (Yield: 91.7%)

$^1$H-NMR (400 MHz, CDCl$_3$) δ 8.67 (s, 1H), 7.96 (s, 1H), 6.68 (s, 1H), 6.36 (d, 1H), 6.25 (t, 1H), 5.74 (d, 1H), 3.83 (m, 9H), 2.83 (t, 4H)

Example 7. Preparation of N-(5-(4-(4-formyl-3-phenyl-1H-pyrazol-1-yl)pyrimidin-2-ylamino)-4-methoxy-2-morpholinophenyl)acrylamide (Compound 2)

A mixture of N-(5-amino-4-methoxy-2-morpholinophenyl)acrylamide (0.2 g, 0.721 mmol), tetrahydrofuran (2.0 mL), 1-(2-chloropyrimidin-4-yl)-3-phenyl-1H-pyrazole-4-carbaldehyde (0.2 g, 0.721 mmol), tris(dibenzylideneacetone)dipalladium (0.03 g, 0.036 mmol), 4,5-bis(diphenylphosphino)-9,9-dimethylxanthene (0.04 g, 0.072 mmol), and cesium carbonate (0.47 g, 1.442 mmol) was refluxed under stirring for 16 hours. The reaction mixture was cooled to 20-30° C. and then purified water (2.0 mL) was slowly added. The resulting solid was filtered and then dried in vacuo to obtain 0.32 g of the titled compound. (Yield: 84.4%)

$^1$H-NMR (400 MHz, DMSO) δ 10.15 (s, 1H), 9.95 (br, 1H), 9.17 (s, 1H), 8.98 (br, 1H), 8.62 (d, 1H), 8.37 (s, 1H), 8.02 (m, 2H), 7.51 (m, 3H), 7.38 (d, 1H), 6.94 (s, 1H), 6.73 (dd, 1H), 6.30 (d, 1H), 5.80 (d, 1H), 3.90 (s, 3H), 3.82 (t, 4H), 2.86 (t, 4H)

Example 8. Preparation of N-(5-(4-(4-formyl-3-phenyl-1H-pyrazol-1-yl)pyrimidin-2-ylamino)-4-methoxy-2-morpholinophenyl)acrylamide (Compound 2)

A mixture of N-(5-amino-4-methoxy-2-morpholinophenyl)acrylamide (1.0 g, 3.606 mmol), 1-(2-chloropyrimidin-4-yl)-3-phenyl-1H-pyrazole-4-carbaldehyde (1.0 g, 3.512 mmol), butanol (15 mL), and conc. hydrochloric acid (0.03 mL, 0.361 mmol) was stirred at about 80° C. for 16 hours. The reaction mixture was cooled to 50° C. and then ethyl acetate (20.0 mL) was slowly added thereto. The resulting solid was filtered and then dried in vacuo to obtain 1.23 g of the titled compound. (Yield: 64.9%)

$^1$H-NMR (400 MHz, DMSO) δ 10.15 (s, 1H), 9.95 (br, 1H), 9.17 (s, 1H), 8.98 (br, 1H), 8.62 (d, 1H), 8.37 (s, 1H), 8.02 (m, 2), 7.51 (m, 3H), 7.38 (d, 1H), 6.94 (s, 1H), 6.73 (dd, 1H), 6.30 (d, 1H), 5.80 (d, 1H), 3.90 (s, 3H), 3.82 (t, 4H), 2.86 (t, 4H)

Example 9. Preparation of N-(5-(4-(4-formyl-3-phenyl-1H-pyrazol-1-yl)pyrimidin-2-ylamino)-4-methoxy-2-morpholinophenyl)acrylamide (Compound 2)

A mixture of tert-butyl (5-acrylamido-2-methoxy-4-morpholinophenyl)carbamate (0.25 g, 0.662 mmol), 1-(2-chloropyrimidin-4-yl)-3-phenyl-1H-pyrazole-4-carbaldehyde (0.20 g, 0.702 mmol), butanol (2 mL), and conc. hydrochloric acid (0.08 mL, 0.066 mmol) was stirred at about 80° C. for 16 hours. The reaction mixture was cooled to 50° C. and then ethyl acetate (20.0 mL) was slowly added thereto. The resulting solid filtered and then dried in vacuo to obtain 0.2 g of the titled compound. (Yield: 57.4%)

$^1$H-NMR (400 MHz, DMSO) δ 10.15 (s, 1H), 9.95 (br, 1H), 9.17 (s, 1H), 8.98 (br, 1H), 8.62 (d, 1H), 8.37 (s, 1H), 8.02 (m, 2), 7.51 (m, 3H), 7.38 (d, 1H), 6.94 (s, 1H), 6.73 (dd, 1H), 6.30 (d, 1H), 5.80 (d, 1H), 3.90 (s, 3H), 3.82 (t, 4H), 2.86 (t, 4H)

Example 10. Preparation of N-(5-(4-(4-((dimethylamino)methyl)-3-phenyl-1H-pyrazol-1-yl)pyrimidin-2-ylamino)-4-methoxy-2-morpholinophenyl)acrylamide (Compound 1)

A mixture of N-(5-(4-(4-formyl-3-phenyl-1H-pyrazol-1-yl)pyrimidin-2-ylamino)-4-methoxy-2-morpholinophenyl)acrylamide (3.0 g, 0.006 mol), dimethylacetamide (30.0 mL), dimethylamine hydrochloride (0.9 g, 0.011 mol), and diisopropylethylamine (3.7 g, 0.029 mol) was stirred at 20-30° C. for 1 hour. Sodium triacetoxyborohydride (3.6 g, 0.017 mol) was added to the reaction mixture, which was then stirred at 20-30° C. for 1 hour. Purified water (30.0 mL) was added to the reaction mixture, which was then stirred for 1 hour. The resulting solid was filtered under reduced pressure and then dried in vacuo to obtain 2.9 g of the titled compound. (Yield: 92.0%)

$^1$H-NMR (400 MHz, DMSO) δ 9.15 (s, 2H), 9.08 (s, 1H), 8.54 (d, 1H), 8.18 (s, 1H), 8.05 (d, 2H), 7.48 (m. 2H), 7.36 (m, 1H), 7.34 (d, 1H), 6.96 (s, 1H), 6.74 (q, 1H), 6.44 (d, 1H), 5.85 (d, 1H), 3.91 (s, 3H), 3.82 (s, 4H), 3.46 (1s, 1H), 2.86 (s, 4H), 2.21 (s, 6H)

The invention claimed is:

1. A process for preparing N-(5-(4-(4-formyl-3-phenyl-1H-pyrazol-1-yl)pyrimidin-2-ylamino)-4-methoxy-2-morpholinophenyl)acrylamide, the process comprising reacting tert-butyl (5-acrylamido-2-methoxy-4-morpholinophenyl)carbamate or N-(5-amino-4-methoxy-2-morpholinophenyl)acrylamide with a compound of Formula 13:

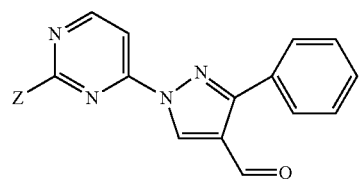

<Formula 13> wherein, Z is halogen.

2. The process according to claim 1, wherein the N-(5-amino-4-methoxy-2-morpholinophenyl)acrylamide is obtained by reacting tert-butyl (5-acrylamido-2-methoxy-4-morpholinophenyl)carbamate with an acid.

3. The process according to claim 2, wherein the acid is one or more selected from the group consisting of hydrochloric acid, sulfuric acid, phosphoric acid, nitric acid, acetic acid, formic acid, sulfonic acid and p-toluenesulfonic acid.

4. The process according to claim 1, wherein the reacting of tert-butyl (5-acrylamido-2-methoxy-4-morpholinophenyl)carbamate with the compound of Formula 13 is carried out in the presence of an acid.

5. The process according to claim 4, wherein the acid is one or more selected from the group consisting of hydrochloric acid, sulfuric acid, phosphoric acid, nitric acid, acetic acid, formic acid, sulfonic acid and p-toluenesulfonic acid.

6. The process according to claim 1, wherein the reacting of the N-(5-amino-4-methoxy-2-morpholinophenyl)acrylamide with the compound of Formula 13 is carried out in the presences of a metal catalyst, a ligand, and a base.

7. The process according to claim 6, wherein the metal catalyst is one or more selected from the group consisting of palladium, copper, iron, cadmium, zinc, and nickel.

8. The process according to claim 7, wherein the metal catalyst is palladium acetate, palladium acetylacetonate, bis(dibenzylideneacetone)palladium, or tris(dibenzylideneacetone)dipalladium.

9. The process according to claim 6, wherein the ligand is one or more selected from the group consisting of 2,2'-bis(diphenylphosphino)-1,1'-binaphthalene, 1,1'-bis(diphenylphosphino)ferrocene, and 4,5-bis(diphenylphosphino)-9,9-dimethylxanthene.

10. The process according to claim 6, wherein the base is one or more selected from the group consisting of potassium tert-butoxide, sodium hydroxide, potassium hydroxide, sodium hydride, sodium carbonate, potassium carbonate, potassium phosphate, sodium phosphate, cesium carbonate, 1,8-diazabicyclo[5.4.0]undec-7-ene, 1,4-diazabicyclo[2.2.2]octane, 1,5-diazabicyclo[4.3.0]non-5-ene, pyridine, triethylamine, diisopropylamine, and diisopropylethylamine.

11. The process according to claim 1, wherein the reacting of N-(5-amino-4-methoxy-2-morpholinophenyl)acrylamide with the compound of Formula 13 is carried out in the presence of an acid.

12. The process according to claim 11, wherein the acid is one or more selected from the group consisting of hydrochloric acid, sulfuric acid, phosphoric acid, nitric acid, acetic acid, formic acid, sulfonic acid and p-toluenesulfonic acid.

13. The process according to claim 1, wherein the tert-butyl (5-acrylamido-2-methoxy-4-morpholinophenyl)carbamate is obtained by a process comprising
(i) reacting tert-butyl (5-amino-2-methoxy-4-morpholinophenyl)carbamate with a compound of Formula 11 to form a compound of Formula 5; and
(ii) reacting the compound of Formula 5 with a base to obtain tert-butyl (5-acrylamido-2-methoxy-4-morpholinophenyl)carbamate:

<Formula 11>

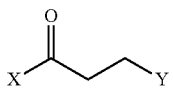

<Formula 5>

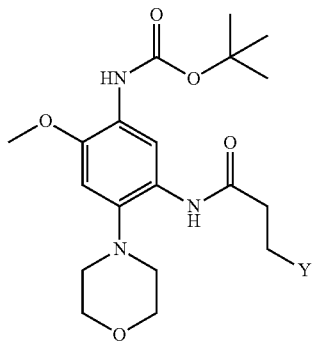

wherein, X and Y are, independently of each other, halogen.

14. The process according to claim 13, wherein Step (i) and Step (ii) are carried out in a one-pot reaction without isolating the compound of Formula 5.

15. The process according to claim 13, wherein the reacting of Step (i) or the reacting of Step (ii) is carried out in the presence of one or more base(s) selected from the group consisting of potassium tert-butoxide, sodium hydroxide, potassium hydroxide, lithium hydroxide, sodium hydride, sodium carbonate, sodium bicarbonate, potassium carbonate, potassium phosphate, sodium phosphate, 1,8-diazabicyclo[5.4.0]undec-7-ene, 1,4-diazabicyclo[2.2.2]octane, 1,5-diazabicyclo[4.3.0]non-5-ene, pyridine, triethylamine, diisopropylamine and diisopropylethylamine.

16. The process according to claim 13, wherein the tert-butyl (5-amino-2-methoxy-4-morpholinophenyl)carbamate is obtained by performing a reduction of tert-butyl (2-methoxy-4-morpholino-5-nitrophenyl)carbamate.

17. The process according to claim 16, wherein the reduction is carried out with a reducing agent selected from the group consisting of formic acid and ammonium formate.

18. The process according to claim 16, wherein the reduction is carried out in the presence of a catalyst selected from the group consisting of palladium, palladium/carbon, zinc, copper, magnesium, and platinum.

19. The process according to claim 16, wherein the tert-butyl (2-methoxy-4-morpholino-5-nitrophenyl)carbamate is obtained by reacting tert-butyl (4-fluoro-2-methoxy-5-nitrophenyl)carbamate with morpholine.

20. The process according to claim 19, wherein the reacting is carried out in the presence of one or more base(s) selected from the group consisting of sodium hydride, sodium $C_1$~$C_6$ alkoxide, potassium $C_1$~$C_6$ alkoxide, sodium carbonate, potassium carbonate, lithium carbonate, cesium carbonate, sodium bicarbonate, potassium bicarbonate, potassium phosphate, 1,8-diazabicyclo[5.4.0]undec-7-ene, 1,4-diazabicyclo[2.2.2]octane, 1,5-diazabicyclo[4.3.0]non-5-ene, pyridine, dimethylaminopyridine, triethylamine, and diisopropylethylamine.

21. The process according to claim 19, wherein the tert-butyl (4-fluoro-2-methoxy-5-nitrophenyl)carbamate is obtained by reacting 4-fluoro-2-methoxy-5-nitroaniline with dibutyl dicarbonate.

22. The process according to claim 1, wherein the compound of Formula 13 is obtained by reacting a compound of Formula 14 with 3-phenyl-1H-pyrazole-4-carbaldehyde:

<Formula 14>

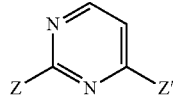

wherein, Z and Z' are, independently of each other, halogen.

23. A compound, wherein said compound is N-(5-amino-4-methoxy-2-morpholinophenyl)acrylamide.

24. A compound, wherein said compound is tert-butyl (5-acrylamido-2-methoxy-4-morpholinophenyl)carbamate.

25. A compound of Formula 5 or salt thereof:
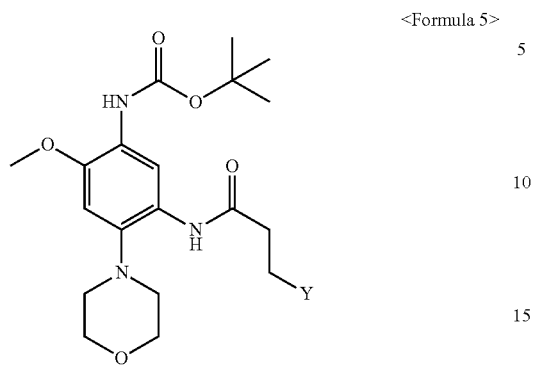
<Formula 5>
wherein, Y is halogen.
26. A compound, wherein said compound is tert-butyl (5-amino-2-methoxy-4-morpholinophenyl)carbamate.
27. A compound, wherein said compound is tert-butyl (2-methoxy-4-morpholino-5-nitrophenyl)carbamate.
* * * * *